(12) United States Patent
Troger et al.

(10) Patent No.: US 8,317,862 B2
(45) Date of Patent: Nov. 27, 2012

(54) METHOD FOR REPLACING A LIGAMENT IN A KNEE

(76) Inventors: Marcus Troger, Isernhagen (DE); Jens Agneskirchner, Pattensen (DE)

( * ) Notice: Subject to any disclaimer, the term of this patent is extended or adjusted under 35 U.S.C. 154(b) by 333 days.

(21) Appl. No.: 12/575,530

(22) Filed: Oct. 8, 2009

(65) Prior Publication Data

US 2010/0121447 A1    May 13, 2010

Related U.S. Application Data

(60) Provisional application No. 61/104,431, filed on Oct. 10, 2008.

(51) Int. Cl.
 *A61F 5/04* (2006.01)
 *A61F 2/08* (2006.01)
(52) U.S. Cl. ............ 623/13.11; 606/96; 606/97; 606/98
(58) Field of Classification Search ...... 623/13.11–13.2; 606/86 R–90, 96, 98, 97
See application file for complete search history.

(56) References Cited

U.S. PATENT DOCUMENTS

| | | |
|---|---|---|
| 4,744,353 A | 5/1988 | McFarland |
| 4,883,048 A | 11/1989 | Purnell |
| 4,911,153 A | 3/1990 | Border |
| 4,922,897 A | 5/1990 | Sapega |
| 5,112,335 A | 5/1992 | Laboureau |
| 5,112,337 A | 5/1992 | Paulos |
| 5,163,940 A | 11/1992 | Bourque |
| 5,242,444 A | 9/1993 | MacMillan |
| 5,306,278 A | 4/1994 | Dahl |
| 5,324,296 A | 6/1994 | Laboureau |
| 5,334,205 A | 8/1994 | Cain |
| 5,350,383 A | 9/1994 | Schmieding |
| 5,354,300 A | 10/1994 | Goble |
| 5,385,567 A | 1/1995 | Goble |
| 5,458,602 A | 10/1995 | Goble |
| 5,562,664 A | 10/1996 | Durlacher |
| 5,643,273 A | 7/1997 | Clark |
| 5,688,284 A | 11/1997 | Chervitz |
| RE36,020 E | 12/1998 | Moore |
| 5,849,013 A | 12/1998 | Whittaker |
| 5,891,150 A | 4/1999 | Chan |
| 5,895,425 A | 4/1999 | Grafton |

(Continued)

FOREIGN PATENT DOCUMENTS

WO    WO 2006125009 A2    11/2006

OTHER PUBLICATIONS

Whittaker, Gregory R., U.S. Appl. No. 60/275,431.

(Continued)

*Primary Examiner* — Thomas J Sweet
*Assistant Examiner* — Yashita Sharma

(57) ABSTRACT

A method of providing a replacement anterior cruciate ligament (ACL) provides a tibial tunnel and at least one femoral tunnel for receiving the replacement ligament, the femoral and tibial tunnels not being colinear but rather in an orientation that more closely mimics the natural ACL. The femoral tunnel is formed through the anterior medial portal. A cross pinning guide having a femoral rod for insertion into the femoral tunnel, a spaced apart arc shaped track and a guide block having one or more bores aligned with the femoral rod whereby an instrument inserted through one of the bores creates a pilot hole for the cross pin which intersects the femoral tunnel and an appropriate angle thereof which avoids ligaments and other sensitive tissue can be selected by adjusting the guide block along the track.

9 Claims, 6 Drawing Sheets

U.S. PATENT DOCUMENTS

| | | | |
|---|---|---|---|
| 5,918,604 A | 7/1999 | Whelan |
| 5,968,050 A | 10/1999 | Torrie |
| 6,019,767 A | 2/2000 | Howell |
| 6,022,356 A | 2/2000 | Noyes |
| 6,066,173 A | 5/2000 | McKernan |
| 6,113,604 A | 9/2000 | Whittaker |
| 6,132,433 A | 10/2000 | Whelan |
| 6,187,011 B1 | 2/2001 | Torrie |
| 6,254,604 B1 | 7/2001 | Howell |
| 6,254,605 B1 | 7/2001 | Howell |
| 6,254,606 B1 | 7/2001 | Carney |
| 6,342,056 B1 | 1/2002 | Mac-Thiong |
| 6,371,124 B1 | 4/2002 | Whelan |
| 6,379,384 B1 | 4/2002 | McKernan |
| 6,514,253 B1 | 2/2003 | Yao |
| 6,517,546 B2 | 2/2003 | Whittaker |
| 6,530,929 B1 | 3/2003 | Justis |
| 6,537,319 B2 | 3/2003 | Whelan |
| 6,540,783 B1 | 4/2003 | Whittaker |
| 6,623,524 B2 | 9/2003 | Schmieding |
| 6,673,076 B2 | 1/2004 | Delogé |
| 6,716,217 B2 | 4/2004 | McKernan |
| 6,733,529 B2 | 5/2004 | Whelan |
| 6,746,453 B2 | 6/2004 | Delogé |
| 6,755,838 B2 | 6/2004 | Trnka |
| 6,783,535 B2 | 8/2004 | Delogé |
| 6,918,916 B2 | 7/2005 | Göbel |
| 6,958,067 B2 | 10/2005 | Whittaker |
| 7,008,422 B2 | 3/2006 | Foley |
| 7,011,660 B2 | 3/2006 | Sherman |
| 7,056,340 B2 | 6/2006 | McKernan |
| 7,066,956 B2 | 6/2006 | Schmieding |
| 7,077,863 B2 | 7/2006 | Schmieding |
| 7,175,631 B2 | 2/2007 | Wilson |
| 7,175,632 B2 | 2/2007 | Singhatat |
| 7,175,633 B2 | 2/2007 | Roth |
| 7,182,766 B1 | 2/2007 | Mogul |
| 7,188,626 B2 | 3/2007 | Foley |
| 7,192,431 B2 | 3/2007 | Hangody |
| 7,192,432 B2 | 3/2007 | Wetzler |
| 7,195,642 B2 | 3/2007 | McKernan |
| 7,201,756 B2 | 4/2007 | Ross |
| 7,229,448 B2 | 6/2007 | Goble |
| 7,238,189 B2 | 7/2007 | Schmieding |
| 7,270,666 B2 | 9/2007 | Lombardo |
| 7,341,592 B1 | 3/2008 | Walters |
| 7,491,206 B2 | 2/2009 | Whittaker |
| 7,575,578 B2 | 8/2009 | Wetzler |
| 7,578,824 B2 | 8/2009 | Justin |
| 7,594,917 B2 | 9/2009 | Whittaker |
| 2003/0220651 A1 | 11/2003 | Pusnik |
| 2004/0015237 A1 | 1/2004 | Whittaker |
| 2004/0059415 A1 | 3/2004 | Schmieding |
| 2004/0082959 A1 | 4/2004 | Hayes |
| 2004/0194789 A1 | 10/2004 | Whelan |
| 2004/0199163 A1 | 10/2004 | Whittaker |
| 2004/0210232 A1 | 10/2004 | Patel |
| 2004/0254585 A1 | 12/2004 | Whittaker |
| 2004/0267273 A1 | 12/2004 | Whittaker |
| 2005/0010289 A1 | 1/2005 | McKernan |
| 2005/0143831 A1 | 6/2005 | Justin |
| 2005/0177171 A1 | 8/2005 | Wetzler |
| 2005/0234469 A1 | 10/2005 | Whittaker |
| 2006/0129162 A1 | 6/2006 | McKernan |
| 2006/0271059 A1 | 11/2006 | Reay Young |
| 2007/0055286 A1 | 3/2007 | Ralph |
| 2007/0083210 A1 | 4/2007 | Hestad |
| 2007/0100346 A1 | 5/2007 | Wyss |
| 2007/0118136 A1 | 5/2007 | Ek |
| 2007/0123896 A1 | 5/2007 | Wyss |
| 2007/0123902 A1 | 5/2007 | Berberich |
| 2007/0191853 A1 | 8/2007 | Stone |
| 2007/0208356 A1 | 9/2007 | Cerundolo |
| 2007/0213819 A1 | 9/2007 | McKernan |
| 2007/0233128 A1 | 10/2007 | Schmieding |
| 2007/0233150 A1 | 10/2007 | Blain |
| 2007/0233151 A1 | 10/2007 | Chudik |
| 2007/0250067 A1 | 10/2007 | Schmieding |
| 2007/0270877 A1 | 11/2007 | Park |
| 2008/0103506 A1 | 5/2008 | Volpi |
| 2009/0157081 A1 | 6/2009 | Homan |
| 2009/0171360 A1 | 7/2009 | Whelan |
| 2009/0228017 A1 | 9/2009 | Collins |
| 2010/0057142 A1 | 3/2010 | Whittaker et al. |

OTHER PUBLICATIONS

Whittaker, Gregory R., U.S. Appl. No. 10/404,685.
Whittaker, Gregory R., U.S. Appl. No. 10/436,018.
Whittaker, Gregory R., U.S. Appl. No. 10/436,038.
Whittaker, Gregory R., U.S. Appl. No. 11/088,250.
Daniel J. McKernan, U.S. Appl. No. 11/343,141.

METHOD FOR REPLACING A LIGAMENT IN A KNEE

This application claims the priority benefit of U.S. Provisional Application No. 61/104,431, filed Oct. 10, 2008, the entire contents of which are hereby incorporated by reference.

FIELD OF THE INVENTION

The invention relates generally to orthopedic surgery and specifically to arthroscopic repair of soft tissue injuries.

BACKGROUND OF THE INVENTION

The complete or partial detachment of a ligament, tendon or other soft tissue from an associated bone within the body is a relatively commonplace injury. Tissue detachment may occur as the result of an accident such as a fall, overexertion during a work-related activity, during the course of an athletic event, or in any one of many other situations or activities. Such injuries are generally the result of excess stress being placed on the tissues.

In the case of a partial detachment, commonly referred to as a "sprain", the injury frequently heals itself, if given sufficient time and if care is taken not to expose the injury to undue stress while healing. If, however, the ligament or tendon is completely detached from its associated bone or bones, or if it is severed as the result of a traumatic injury, partial or permanent disability may result. Fortunately, a number of surgical procedures exist for re-attaching such detached tissues, as well as for completely replacing severely damaged tissues with grafts that may be formed from tissue harvested from elsewhere in the patient's body (an autograft), from another human (an allograft) or from an animal (a xenograft), or may be synthetic in origin.

A damaged anterior cruciate ligament ("ACL") in a human knee is commonly replaced with a graft ligament by first forming bone tunnels in the tibia ("tibial tunnel") and femur (femoral tunnel") at nominally the points of normal attachment of the native ACL. An end of the graft ligament (which may, but not necessarily terminate in a bone block) is passed through the tibial tunnel and into the femoral tunnel, positioning the graft to span the joint space in the knee between the tunnels. The ends of the graft are then fixed in the respective tunnels. Several methods and devices for fixing the graft ligament in the femoral and tibial tunnels are known, including various types of ligament or suture anchors, buttons and staples for attaching objects to bone.

One known method for anchoring bone blocks in bone tunnels is through "cross-pinning", in which a pin, screw or rod is inserted into the bone, transversely to the bone tunnel, so as to intersect the graft ligament (or bone block, if present), to "cross-pin" the graft in the bone tunnel. The cross-pin (i.e., the aforementioned pin, screw or rod) is generally placed in a pre-drilled passageway that is prepared using a drill guide. Methods and apparatus for effecting ACL repairs that include the use of cross-pinning drill guides are disclosed in commonly assigned U.S. Pat. Nos. 5,849,013; 6,066,173; 6,113, 604; 6,379,384; 6,517,546; 6,540,783; 6,716,217; 6,958,067; 7,056,340 and 7,195,642, and U.S. patent application Ser. Nos. 10/404,685; 10/436,018; 10/436,038; 11/088,250 and 11/343,141, the contents of which are hereby incorporated by reference in their entirety.

Considerations for cross-pinning graft ligaments in the tibia differ from considerations for cross-pinning of graft ligaments in the femur. These considerations include differences in anatomical geometry, bone quality, and other considerations. These different requirements generally result in the development and application of different cross-pinning guides for femoral and tibial cross-pinning, adding complexity and expense to the performance of ACL replacement surgeries. Further, native ACLs include two functionally distinct components, the anteromedial and posterolateral bundles, and fully anatomic reconstructions of an ACL to restore the kinematics of a natural knee joint may require separate tunnels to be drilled and potentially cross-pinned for each component of the ACL, further increasing the complexity of the surgery and the requirement for multiple cross-pinning guides.

In addition, known femoral cross-pinning guides and methods for their application generally require that the femoral and tibial tunnels are substantially aligned with one another, so that a portion of the femoral guide can be passed linearly through the tibial tunnel and into the femoral tunnel for positioning femoral cross pins. This requirement for substantial alignment of the tibial and femoral tunnels does not necessarily provide optimal positioning of the replacement ligament, or ligament bundles, thereby limiting the surgeon's ability to provide fully anatomical positioning of a replacement ACL.

Accordingly, there exists a need for improved methods and apparatus for anatomical replacement of an ACL ligament in a knee.

SUMMARY OF THE INVENTION

The present invention relates to a method for replacing an ACL in a human knee by cross-pinning opposite ends of one or more graft in respective femoral and tibial bone bores. In an aspect of the present invention, the femoral and tibial tunnels have independently established axes and are cross-pinned using a universal cross-pinning guide. In an embodiment, the guide includes interchangeable guide pins for aligning the cross-pinning guide with respective femoral and tibial tunnels. While employing the guide for the femoral tunnel the guide pin used therefor need not also be inserted into the tibial tunnel.

In another aspect of the invention, a method for performing an ACL replacement using two ACL graft bundles is provided. In this method, two femoral and two tibial tunnels are provided, and the universal cross-pinning guide is used to guide the cross-pinning of graft ligament portions in each bone bore. In yet another aspect of the present invention, a tibial tunnel for cross-pinning is provided from outside the body, through the tibia and into the joint space between the tibia and the femur, while the femoral tunnel for cross-pinning is provided from within the joint space, into and at least partially through the femur.

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
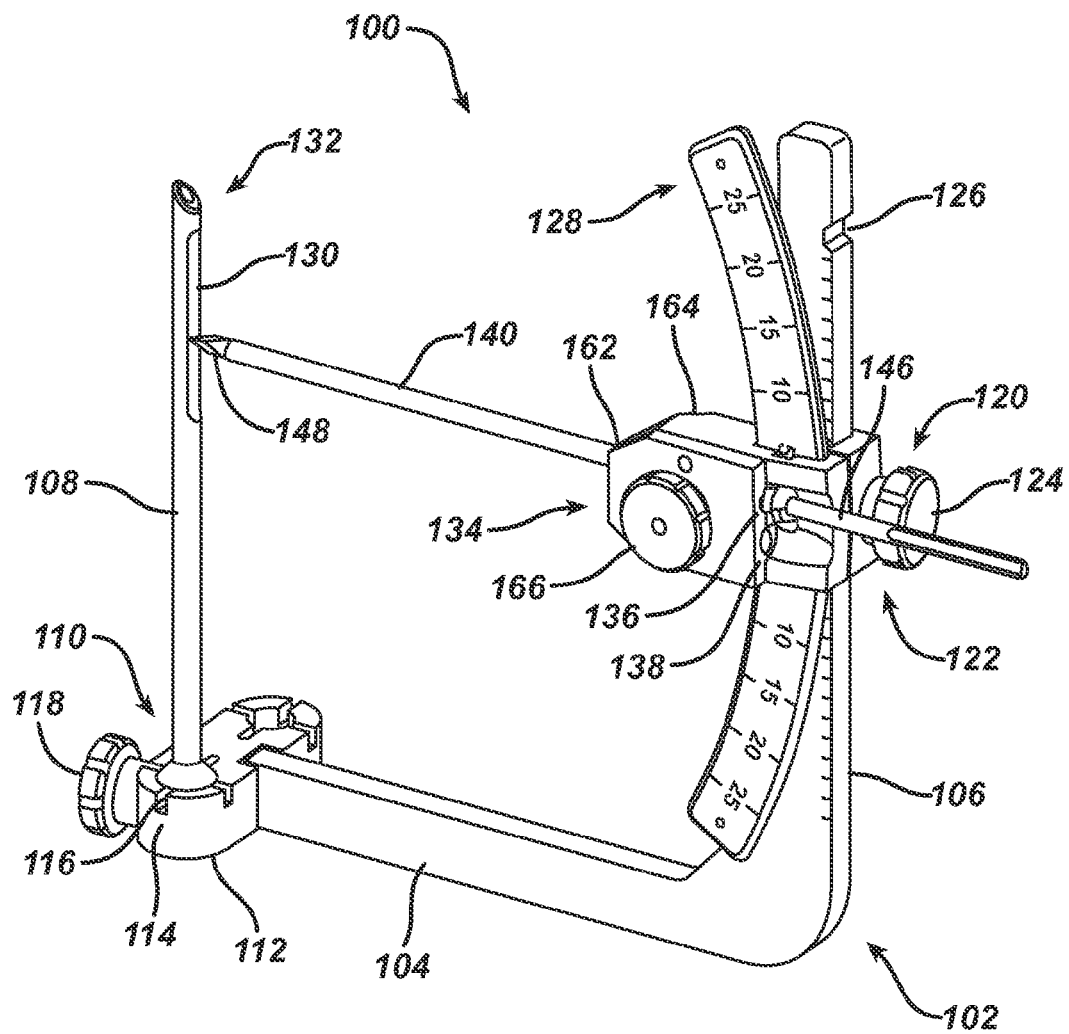
FIG. 1 is a perspective view of a cross-pinning guide according to the present invention, for use in cross-pinning a graft in a tibial tunnel or in a femoral tunnel.
Figure 2:
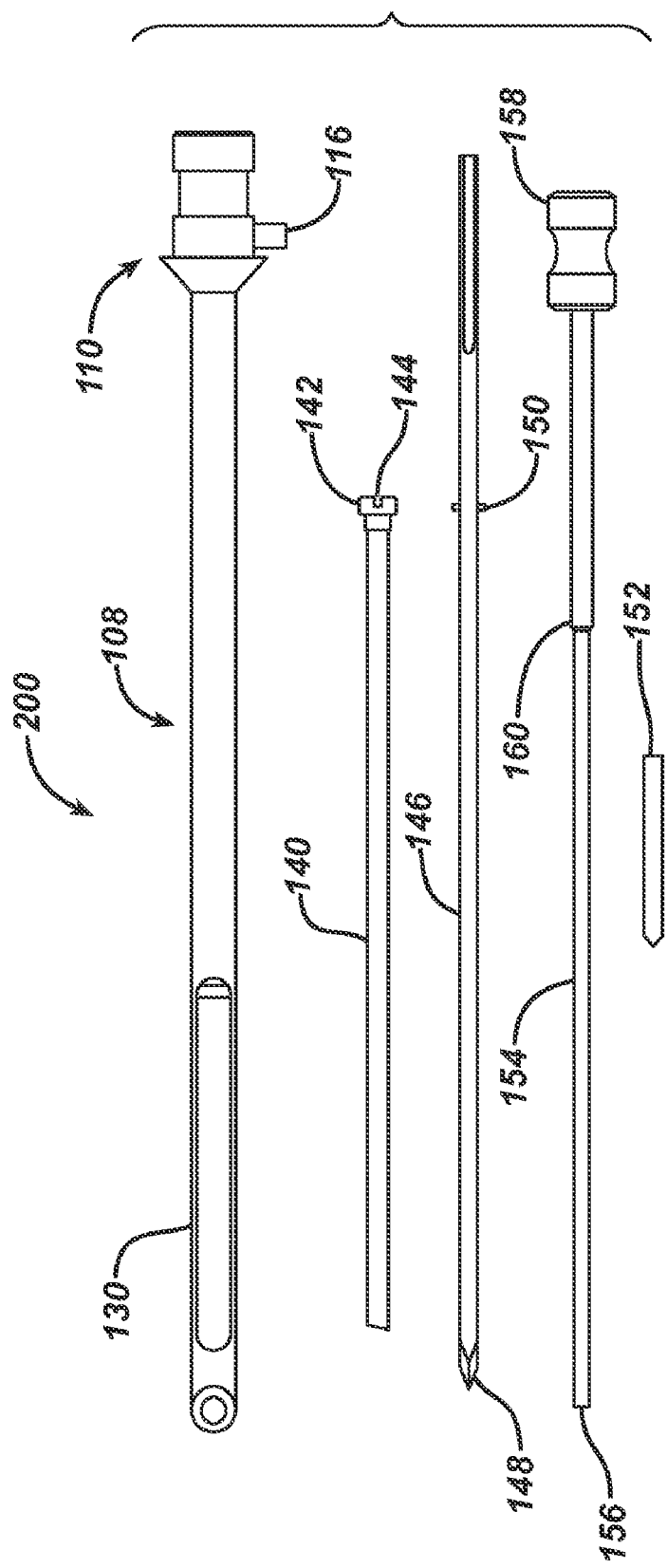
FIG. 2 is a side elevation view of components and tools used with the cross-pinning guide of FIG. 1.

Referring more particularly to the figures, FIG. 1 illustrates a cross-pinning guide 100 for use according to a method of the present invention, for cross-pinning an ACL graft in a bone tunnel, for example, in either a tibial tunnel or a femoral tunnel in a knee joint. Turning also to FIG. 2, a number of components and tools 200 are associated with the cross-pinning guide 100, as referenced hereinbelow. The cross-pin guide 100 comprises an L-shaped member 102 having a base 104 and an arm 106. The arm 106 extends transversely to, and preferably normal to the base 104. In an embodiment, the arm 106 is provided with a ruled scale along at least a portion of its length.

An interchangeable tunnel guide rod 108 is removably mountable to the base 104, near a first end 110 of the guide rod 108, and oriented parallel to the arm 106. The guide rod 108 is preferably provided to a surgeon in a kit including a plurality of guide rods 108 having a selection of lengths and diameters to accommodate various graft sizes and patient anatomies. Two mounting holes 112 are provided in the base 104 for receiving the guide rod 108, one of the two mounting holes 112 being for use of the drill guide 100 on a left knee and the other for use on a right knee. The rotational orientation of the guide rod 108 in either mounting hole 112 is fixed via a slot 114 adjacent the respective mounting hole 112, and a mating pin 116 near the first end 110 of the guide rod 108 (see FIG. 2). In a preferred embodiment, the guide rod 108 is cannulated along its length for placement on a guidewire (not shown). The guide rod 108 may be retained in the respective mounting hole 112 via a locking knob 118 that may activate a spring-loaded detent, a retaining screw, or another retention means. In a preferred embodiment, a kit is provided including a plurality of guide rods sized for various locations and sizes of bone tunnels.

The cross-pin guide 100 further comprises an arced rail assembly 120 slidably mounted to the arm 106. The arced rail assembly 120 can be locked in position along the arm 106 using a locking device 122 that in a preferred embodiment includes a knob 124 connected to a locking screw that engages the arm 106 when tightened. The locking screw may also be spring-loaded for positive engagement with one or more detents 126 provided along the arm 106 for preferred positioning of the arced rail assembly 120 along the arm 106.

The arced rail assembly 120 includes an arced rail 128 having a substantially circular arc that is centered about a position within a diametrical, longitudinally-elongated passageway 130 in the tunnel guide rod 108, near a second end 132 of the guide rod 108, opposite the first end 110. On larger diameter sizes of the guide rod 108 the passageway 130 can extend all the way through the guide rod 108. Mounted to and positionable along the arced rail 128 is a guide block 134 that includes two bores 136, 138, each of which can slidably receive a trocar sleeve 140.

One trocar sleeve 140 is shown positioned in the bore 136 in FIG. 1. The second bore 138 provides for placing two cross-pins across a bone tunnel. Descriptions herein for the installation of one cross-pin intersecting a bone tunnel apply equally to the installation of two cross-pins intersecting the bone tunnel. The trocar sleeve 136 is axially and rotatably movable in the bore 136 and, as also illustrated in FIG. 2, is provided with a collar portion 142 having a diametrically extending slot 144 formed therein.

A trocar 146, slidably disposable in the trocar sleeve 140, is provided with a sharp tip 148 for penetration of bone. A transversely-extending pin 150 is provided near, but spaced from, the end of the trocar opposite the sharp tip 148. The pin 150 is fixed in place in the trocar 146 and is received by the slot 144 in the trocar sleeve collar 142 such that axial (in a distal direction) and rotational movement of trocar 146 causes similar movement of sleeve 140, for drilling the trocar 146 and sleeve 140 together into bone. Preferably, the trocar 146 and sleeve 140 are drilled far enough into the bone to enter the passageway 130.

A cross-pin 152 (see FIG. 2) is slidable through the trocar sleeve 140 for insertion into bone using an insertion tool 154. The insertion tool 154 has a cross-pin insertion tip 156, a handle 158 that can be struck with a mallet for inserting the cross pin through the trocar sleeve 140, and a step-in diameter 160 for controlling the depth of insertion of the cross-pin 152. The guide block 134 includes upper 162 and lower 164 components held together via a screw 166 so that the drill guide 100 can be disassembled from the trocar sleeves, leaving the trocar sleeves positioned in bone for insertion of cross-pins. In another preferred embodiment, the guide block 134 is configured for the direct placement of cross-pins, without the use of trocar sleeves and trocars. In this case, the cross-pins are inserted through, and guided by the bores 136, 138 in the guide block.

The present invention can be practiced with cross-pins 152 of any type, and is independent of the type of cross-pins used in a surgical procedure. The cross-pins 152 may be polymeric, a bioceramic, a composite, or made of non-absorbable materials. Preferably, the cross-pins 152 are formed of a bio-absorbable material. Accordingly, the ACL reconstruction will hereinafter be discussed in the context of using absorbable cross-pins, and in the context of using preferred apparatus for deploying such absorbable cross-pins 152. Preferred materials include poly(lactic acid) with tri-calcium phosphate and copolymer of lactide and glycolide (poly(lactide-co-glycolide)) with tri-calcium phosphate.

In an ACL replacement procedure of the present invention, the patient is prepared for arthroscopic knee surgery using standard techniques. An anterolateral (AL) arthroscopic viewing portal is created in the patient's knee, as well as an anteromedial (AM) working portal. These standard surgical portals are not illustrated in the Figures. Also not shown in the Figures are skin incisions required for preparing a tibial tunnel or other steps in an ACL replacement procedure. After confirmation of an ACL tear requiring ligament replacement, a suitable graft is provided, for example, through harvesting a semitendinosus graft from the patient, or by providing an allograft, although any type and source of ACL graft can be implanted using the methods of this invention, including soft tissue grafts and grafts terminated with bone blocks or substitute rigid materials.

Figure 3:
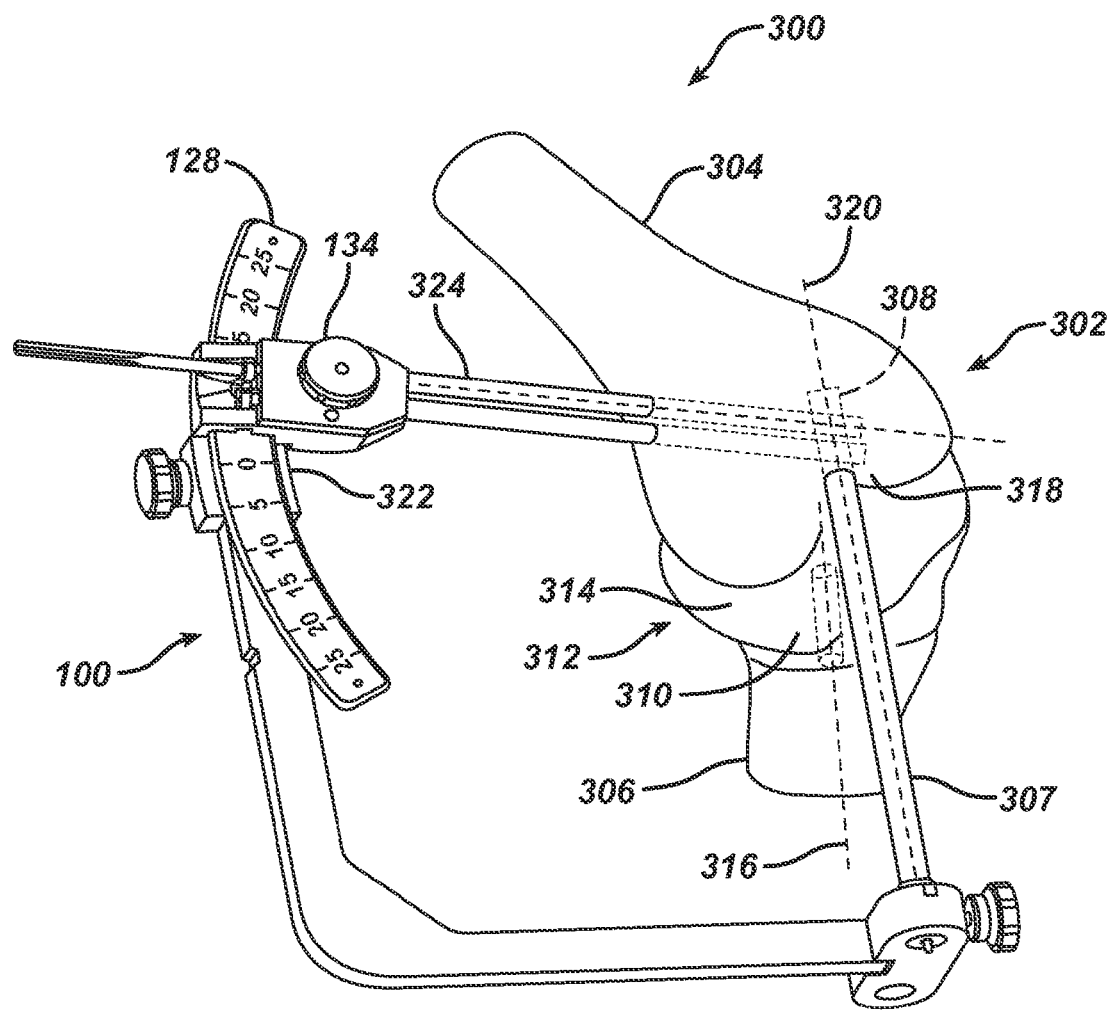
FIG. 3 is a perspective view of the cross-pinning guide of FIG. 1 in use for cross-pinning a femoral bone tunnel prepared via an anteromedial arthroscopic portal.

FIG. 3 schematically illustrates femoral cross-pinning 300 according to the present invention. Referring to FIG. 3, there is shown a human knee joint 302 including a femur 304 and a tibia 306, each prepared according to known surgical methods with a respective femoral tunnel (also known as a femoral tunnel) 308 and tibial tunnel (also known as a tibial tunnel) 310 appropriate for receiving an ACL replacement graft (not shown in FIG. 3), and a joint space 312 between the femur 304 and the tibia 306. The tibial tunnel 310 extends from outside the patient, through an incision in the skin, through the tibia 306 and into the joint space 312 at substantially the native ACL attachment location on the tibial plateau 314. Exemplary of preparation of the tibial tunnel 310, a drill guide known in the art is first used to pass a guide pin along a tibial tunnel axis 316 for the tibial tunnel 310, followed by reaming along the guide pin to a diameter appropriate for receiving the graft.

The femoral tunnel 308 is also prepared using known methods. At a position in the femoral notch 318 that the surgeon determines is appropriate for the insertion of the graft, a guide pin is first drilled into the femur 304 along a selected femoral tunnel axis 320 via the anteromedial (AM) portal, followed by reaming to create a femoral tunnel 308 along the guide pin to an appropriate depth and diameter for receiving the graft. Importantly, preparing the femoral tunnel 308 via the AM portal enables the surgeon to establish the best anatomical position and axis for the femoral tunnel 308, independently of the preparation and position of the tibial tunnel. To better attain kinematically optimal surgical outcomes, two functionally distinct component grafts comprising replacements for native ACL components: the anteromedial and posterolateral bundles, can be independently implanted and cross-pinned using the methods of the present invention, using two bores provided in one or both of the femur and the tibia, and generally using two bores in each of the femur and the tibia. Various guides have been developed for preparing multiple bone bores for these procedures, which are variously referred to as "dual-tunnel," "dual-bundle," "double-bundle" or "double tunnel" procedures. It is to be understood that the methods described herein are equally applicable for cross-pinning grafts or graft components in any number of bone bores during an ACL replacement procedure, whether employing a single ACL replacement graft, or multiple graft components and a correspondingly larger number of bone bores for cross-pinning.

The present invention allows a surgeon to reliably align a proper cross pin orientation into a tunnel formed through the AM portal, which heretofore was difficult or impossible with prior cross pinning guides. With the tibial 310 and femoral 308 tunnels prepared, an appropriately sized femoral guide rod 307 is mounted to the cross-pin guide 100. The guide rod 307 is then inserted through the AM portal into the femoral tunnel 308 only and not inserted into the tibial tunnel. The surgeon chooses a femoral cross-pinning angle to avoid or minimize any damage to soft tissues including but not limited to medial collateral ligament, lateral collateral ligament, popliteal tendon, and quadriceps muscle. The surgeon palpates the knee to locate the cartilage around the joint, and positions the guide head 134 along the arced rail 128 superior to the cartilage. In an embodiment, the guide head 134 is positioned along the arced rail 128 approximately twenty degrees superior to a zero-angle marking 322 on the arced rail 128. Then at least one femoral trocar sleeve 324 is drilled into the femur using the method described hereinabove. Depending on the required repair, the surgeon decides whether the cross-pinning will be done from the medial side (as illustrated in FIG. 3) or the lateral side of the knee joint 302. The cross-pin guide 100 is then removed from the femur 304, leaving the at least one femoral trocar sleeve 324 in place in the femur.

To verify the accuracy of placement of the at least one femoral trocar sleeve 324 in the femur 304, the surgeon can use an arthroscope to look along the femoral tunnel 308 from the joint space 312 while inserting a guide pin (not shown) through the femoral trocar sleeve 324, to visualize the guide pin as it enters the femoral tunnel 308.

Figure 4:
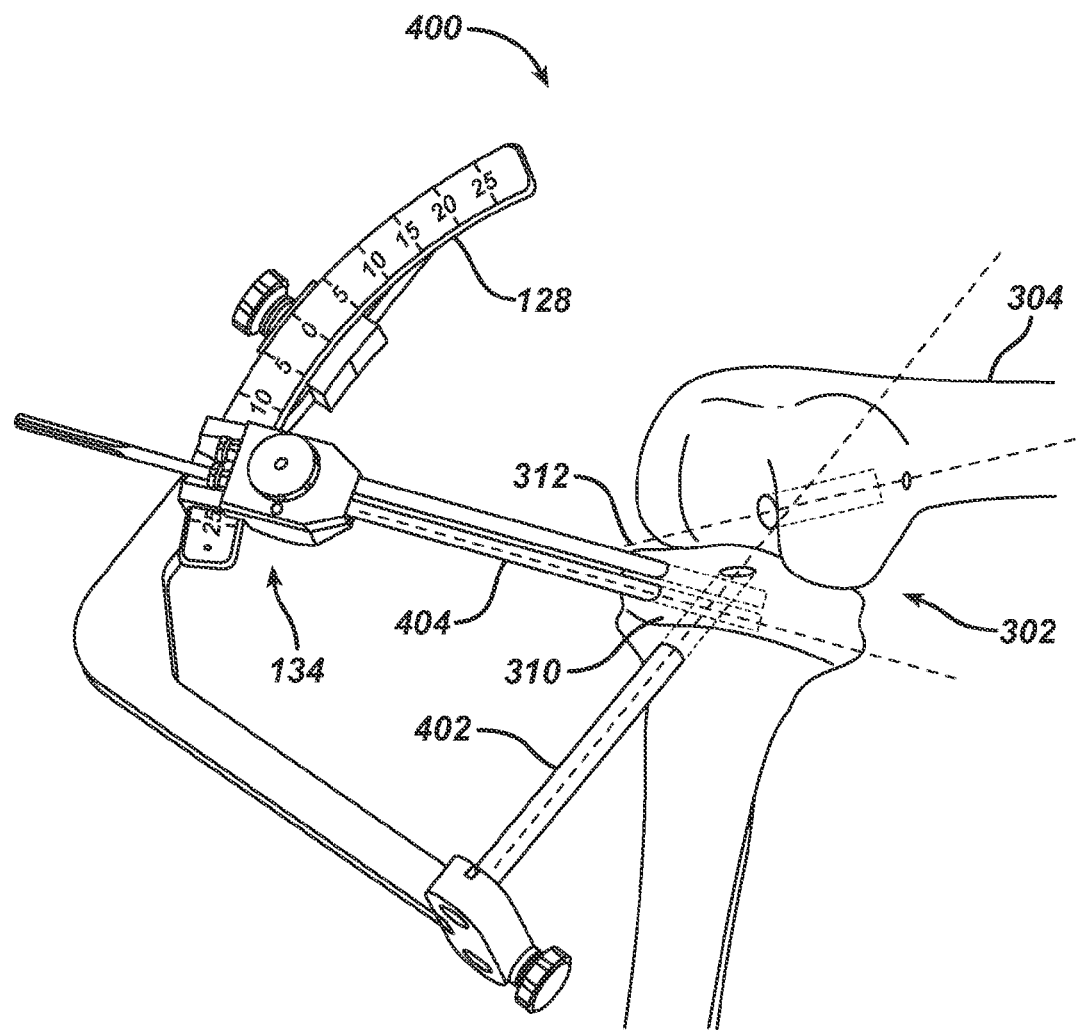
FIG. 4 is a perspective view of the use of the cross-pinning guide of FIG. 1 in use for cross-pinning a tibial bone tunnel.

The femoral guide rod 307 for the femoral tunnel is then unmounted from the cross-pinning guide 100 and replaced with an appropriately-sized tibial guide rod 402 for tibial cross-pinning, as shown in FIG. 4, which illustrates the knee joint 302 from a different perspective from that of FIG. 3. In FIG. 4, the tibial guide rod 402 is inserted into the tibial tunnel 310 from outside the patient toward the joint space 312. Depending on the anatomy of the patient's knee and other factors, the surgeon decides whether the cross-pinning will be done from the medial side (as illustrated in FIG. 4) or the lateral side of the knee joint 302. The surgeon then establishes the correct tibial cross-pinning angle and positions the guide head 134 appropriately along the arced rail 128 inferior to the zero-angle marking 322 on the arced rail. In an embodiment, the guide head 134 is positioned along the arced rail 128 approximately twenty degrees inferior to the zero-angle marking 322 on the arced rail 128. Then at least one tibial trocar sleeve 404 is drilled into the femur using the method described hereinabove. The cross-pin guide 100 is then removed from the tibia 304, leaving the at least one tibial trocar sleeve 404 in place in the tibia.

To verify the accuracy of placement of the at least one tibial trocar sleeve 404 in the femur 304, the surgeon can use an arthroscope to look along the tibial tunnel 310 while inserting a guide pin (not shown) through the trocar sleeve 404, to visualize the guide pin as it enters the tibial tunnel 310.

Figure 5:
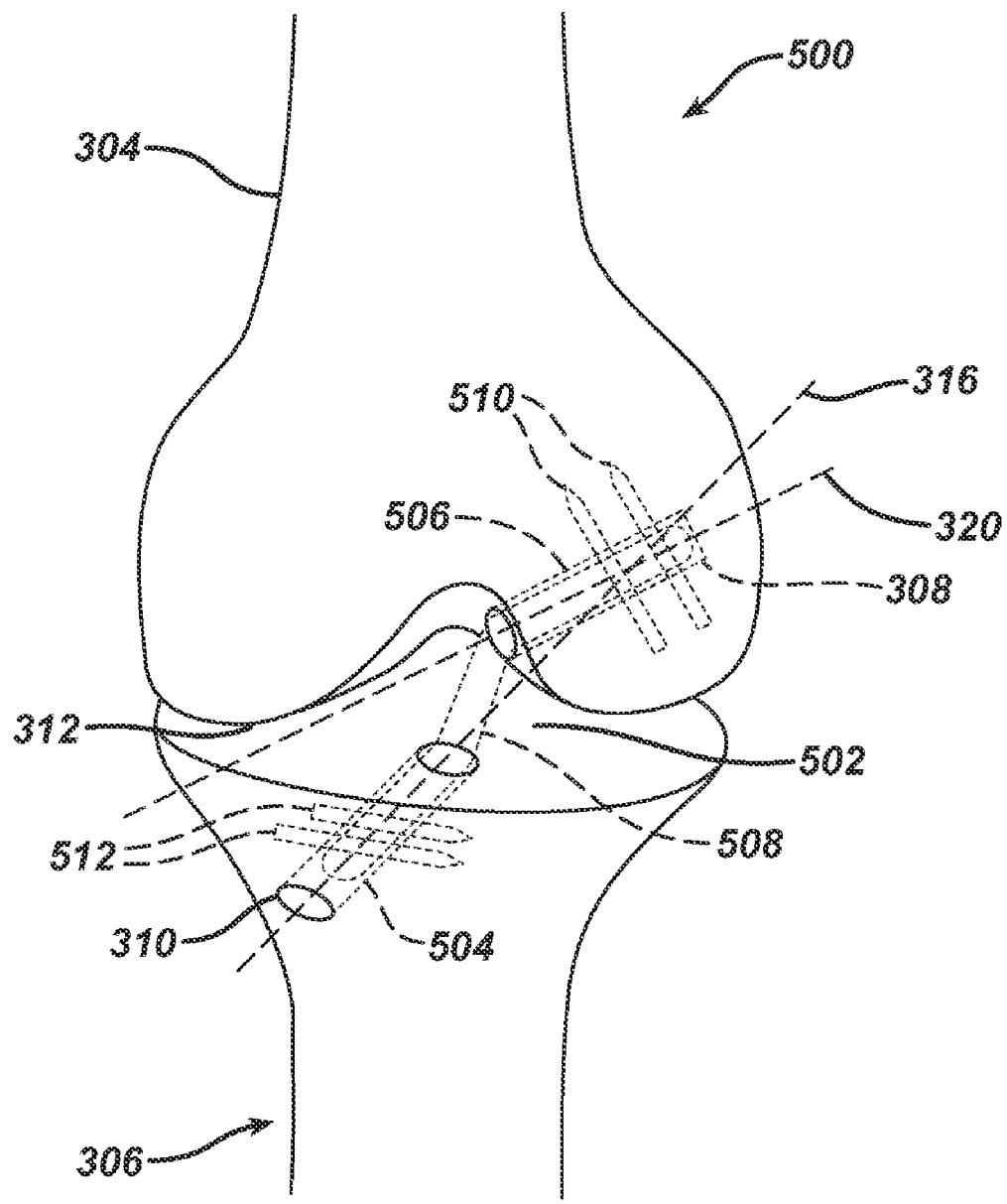
FIG. 5 is a front elevation view of an ACL graft cross-pinned in a knee using methods of the present invention.

FIG. 5 schematically illustrates an example of a single-bundle graft placement 500 in a knee. Referring to FIG. 5, an ACL graft 502 is shown, having a first end portion 504 positioned in the tibial tunnel 310 and a second end portion 506 positioned in the femoral tunnel 308. Referring to FIGS. 3, 4 and 5, once the placement accuracy of the femoral 324 and tibial trocar sleeve 404 has been verified and the graft 502 has been prepared for implantation, a first end portion 504 of the graft (or graft component for a dual bundle procedure) is positioned in the tibial tunnel 310 and a second end portion 506 of the graft 502 is positioned in the femoral tunnel 308. Methods for preparing a graft for implantation and for positioning a graft in a bone bore are well known in this art. For example, the graft may be positioned in a bone bore by using a passing pin, placed through a guide hole formed during the preparation of a bone bore, to pull the graft into the bore via a suture attached between the graft and the passing pin.

The graft 502 can be positioned by passing the second end portion 506 of the graft 502 through the tibial tunnel 310, across the joint space 312 and into the femoral tunnel 308, leaving a central portion 508 of the graft 502 spanning the joint space 312. Alternatively, the graft 502 can be positioned in the femoral 308 and tibial tunnel 310 entirely from the joint space 312, by passing the first end 504 of the graft 502 into the tibial tunnel 310, and passing the second end portion 506 into the femoral tunnel 308, leaving the central portion 508 spanning the joint space 312.

With the graft 502 properly positioned in the knee, one or more femoral cross-pins 510 are then inserted transversely through the second end portion 506 of the graft in the femoral tunnel 308 via a respective trocar sleeve 324 (not shown in FIG. 5) using the insertion tool 154, to fix the graft 502 in the femoral tunnel 308. Once the femoral cross-pin 510 has been satisfactorily positioned in the femoral tunnel 308 and second end portion 506 of the graft 502 for cross-pinning, the respective trocar sleeve is removed from the femur 304. In an alternate embodiment wherein a replacement ACL graft terminates in a bone block, for example, for implanting a bone-tendon-bone (BTB) graft, the an additional drilling step may be required after the graft has been placed in the femoral tunnel 308. This additional drilling step can be performed by passing a stepped-diameter trocar through the respective trocar sleeve positioned in bone for receiving a cross-pin, and through the graft, before inserting the cross-pin.

Once the second end 506 of the graft 502 has been cross-pinned in the femoral tunnel 308, the graft 502 is tensioned along its length, and the first end portion 504 of the graft 502 is cross-pinned in the tibial tunnel 310, using one or more tibial cross pins 512 in the same manner as the second end portion 506 of the graft 502 was cross-pinned in the femoral tunnel 308, to complete the repair. As can be seen clearly in FIG. 5 and discussed hereinabove, the tibial tunnel axis 316 and the femoral tunnel axis 320, having been independently established by the surgeon, can be non-collinear or non-intersecting, to provide optimal positioning for an anatomic replacement of a native ACL. Depending on the position of the knee joint during or post-surgery, the tibial and respective femoral tunnels 310 and 308 for a graft ligament may be in axial or near-axial alignment with one another, despite the respective bores having been independently established during surgery.

Figure 6:
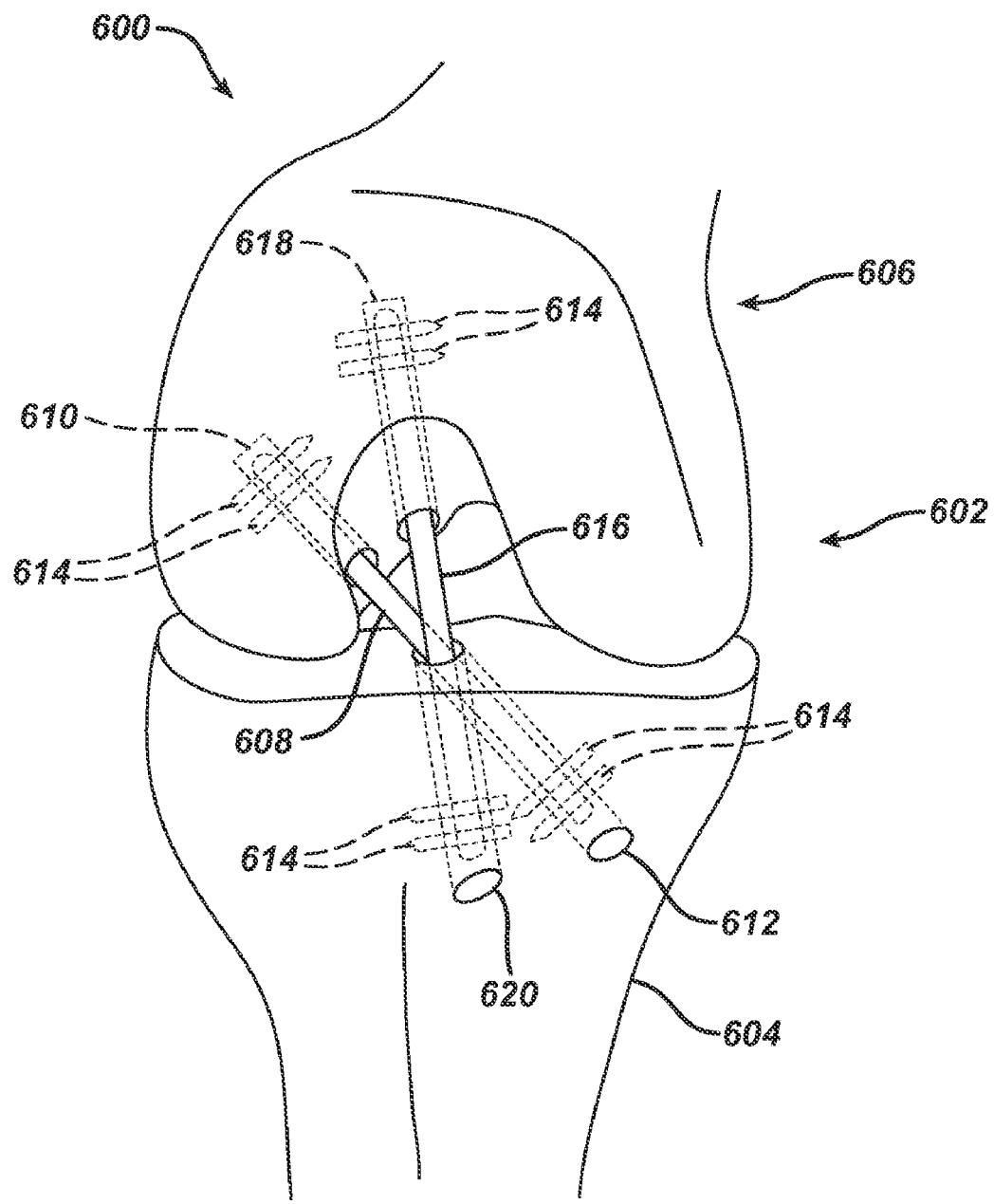
FIG. 6 is a front elevation view of a dual-bundle ACL graft cross-pinned in a knee using methods of the present invention.

The methods of the present invention can be used to perform a dual-bundle ACL replacement surgical procedure. FIG. 6 schematically illustrates an example of a completed dual-bundle graft placement 600 that may be performed in a knee 602 having a tibia 604 and a femur 606. As seen in FIG. 6, an anteromedial graft component 608 is implanted in the knee 602, and fixed in a femoral tunnel 610 and a tibial tunnel 612 using cross-pins 614. A posterolateral graft component 616 is also implanted in the knee 602, and fixed in respective femoral 618 and a tibial 620 bores using cross-pins 614. As illustrated in FIG. 6, two cross-pins 614 are used in each of the bores 610, 612, 618, 620. In another embodiment, one cross-pin 614 is used to fix each of one or more graft component in a respective bore.

The method of the present invention provides several advantages over prior ACL replacement methods. The use of an AM portal for preparing one or more femoral tunnel enables the surgeon to better anatomically place the femoral and tibial tunnels independently of one another, without the constraint of prior cross-pinning repair methods that require the femoral and tibial tunnels to be substantially aligned for receiving a femoral cross-pinning guide that must pass through the tibial tunnel to access the femoral tunnel. In addition, use of a universal cross-pinning guide that can be applied to both tibial and femoral tunnels, provides a unified and simplified surgical instrument set that may enable surgeons to achieve more consistent results and cost reductions for patients.

Further, there is increasing interest in performing ACL replacement surgeries using separate anteromedial and posterolateral replacement ligament components, to provide more closely anatomical and more fully kinematically functional repairs. These double-bundle repairs also generally require additional bone tunnels to be drilled to accommodate the additional graft components. The cross-pinning methods and guide of the present invention enable the surgeon to provide multiple tunnel, cross-pinned graft replacements in a straightforward manner.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for replacing an anterior cruciate ligament in a patient having a femur, a tibia and a joint space therebetween, the method comprising:

a) providing a replacement ligament having a length, a first end portion, a second end portion opposite the first end portion along the length, and a central portion between the first end portion and the second end portion along the length;
b) preparing a tibial tunnel extending through the tibia and into the joint space, the tibial tunnel sized to receive internally the first end portion, the tibial tunnel having a first longitudinal axis;
c) preparing a femoral tunnel which extends from within the joint space, into and at least partially through the femur, the femoral tunnel being sized to receive internally the second end portion of the replacement anterior cruciate ligament, the femoral tunnel having a second longitudinal axis;
d) preparing first and second femoral pilot holes with a cross pinning guide comprising a femoral guide rod, an arm spaced apart from and essentially parallel to the femoral guide rod, an arc shaped rail affixed to the arm and a guide block releasably mounted for travel along the rail and having a first guide bore and a second guide bore parallel to the first guide bore therethrough, the guide bores having guide bore axes therethrough which intersect the femoral guide rod, by inserting the femoral guide rod into the femoral tunnel only and not inserting the femoral guide rod into the tibial tunnel, aligning desired femoral pilot hole axes intersecting the second longitudinal axis by adjusting the guide block along the rail and then via an instrument operated through the first and second guide bores creating the first and second femoral pilot holes;
e) affixing the first end portion of the replacement ligament in the tibial tunnel;
and
f) affixing the second end portion of the replacement anterior cruciate ligament in the femoral tunnel by inserting a first femoral cross pin into the first femoral pilot hole and inserting a second femoral cross pin into the second femoral pilot hole and through the second end portion of the replacement anterior cruciate ligament positioned in the femoral tunnel.

2. A method according to claim 1 wherein the femoral tunnel is prepared through the AM portal.

3. A method according to claim 1 wherein the first longitudinal axis and second longitudinal axis are not common.

4. A method according to claim 1 and further comprising the step of creating a first tibial pilot hole intersecting the tibial tunnel using the cross pinning guide.

5. A method according to claim 4 further comprising the steps of putting a tibial guide rod into the cross pinning guide, and aligning a desired tibial pilot hole axis by adjusting the guide block along the rail.

6. A method according to claim 5 wherein the tibial pilot hole axis is inferior to an axis normal to the first longitudinal axis.

7. A method according to claim 6 where the tibial pilot hole axis is inferior to an axis normal to the first longitudinal axis by about 20 degrees.

8. A method according to claim 1 wherein the femoral pilot hole axis is superior to an axis normal to the second longitudinal axis.

9. A method according to claim 1 and further comprising the steps of creating a second femoral tunnel which extends from within the joint space into and at least partially through the femur; and adjusting the guide block along the rail to provide a desired orientation of a second femoral guide hole to intersect with the second femoral tunnel.

* * * * *